US009003868B2

(12) United States Patent
Ono et al.

(10) Patent No.: US 9,003,868 B2
(45) Date of Patent: Apr. 14, 2015

(54) LIQUID CHROMATOGRAPH AND SAMPLE INTRODUCING APPARATUS

(75) Inventors: Yumiko Ono, Hitachinaka (JP); Kimihiko Ishii, Hitachinaka (JP); Eri Yamashita, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 210 days.

(21) Appl. No.: 13/466,841

(22) Filed: May 8, 2012

(65) Prior Publication Data

US 2012/0279284 A1 Nov. 8, 2012

Related U.S. Application Data

(63) Continuation of application No. 12/235,145, filed on Sep. 22, 2008, now Pat. No. 8,191,404.

(30) Foreign Application Priority Data

Sep. 26, 2007 (JP) ................................. 2007-249613

(51) Int. Cl.
*G01N 30/24* (2006.01)
*G01N 30/34* (2006.01)
*G01N 35/10* (2006.01)

(52) U.S. Cl.
CPC ................ *G01N 30/24* (2013.01); *G01N 30/34* (2013.01); *G01N 35/1097* (2013.01)

(58) Field of Classification Search
CPC .............................. G01N 30/20; G01N 30/24
See application file for complete search history.

(56) References Cited

U.S. PATENT DOCUMENTS

| 7,219,566 | B1 * | 5/2007 | Maeda | ........................... 73/864 |
| 7,555,937 | B2 | 7/2009 | Hirayama et al. | |
| 2006/0186028 | A1 * | 8/2006 | Hughes | ...................... 210/198.2 |
| 2007/0034557 | A1 | 2/2007 | Ito | |

FOREIGN PATENT DOCUMENTS

| JP | 2005-265805 | 9/2005 |
| JP | 2007-121192 | 5/2007 |

OTHER PUBLICATIONS

Entire Prosecution of U.S. Appl. No. 12/235,145 to Yumiko Ono et al., on Sep. 22, 2008 entitles, "Liquid Chromatograph and Sample Introducing Apparatus,".

* cited by examiner

*Primary Examiner* — Paul West
(74) *Attorney, Agent, or Firm* — McDermott Will & Emery LLP (57) ABSTRACT

Disclosed herein is a sample introducing apparatus which is designed such that the analytical flow path runs from the needle to the separation column without the flow path switching means placed at the downstream side of the needle. This design reduces dead volume, which in turn reduces the diffusion of the sample injected into the analytical flow path. Moreover, the absence of the flow path switching means at the downstream side of the needle to inject a sample into the analytical flow path eliminates connection of the pipe with the flow path switching means. This prevents the sample from remaining in the connecting part, thereby reducing sample carry-over and improving the accuracy of analysis.

16 Claims, 12 Drawing Sheets

FIG. 13C ered, the inventors examined how these problems (dead volume deteriorates the accuracy of analysis. "Dead volume" means any space which exists in the flow from sample introduction to detection in the liquid chromatograph and which is useless, or rather harmful, to sample separation and hence is undesirable.

LIQUID CHROMATOGRAPH AND SAMPLE INTRODUCING APPARATUS

RELATED APPLICATIONS

This application is a Continuation of U.S. application Ser. No. 12/235,145, filed on Sep. 22, 2008 now U.S. Pat. No. 8,191,404, claiming priority of Japanese Patent Application No. 2007-249613, filed on Sep. 26, 2007, the entire contents of each of which are hereby incorporated by reference.

BACKGROUND OF THE INVENTION

1. Field of the Invention

The present invention relates to a liquid chromatograph and a sample introducing apparatus therefor.

2. Description of the Related Art

Figure 1:
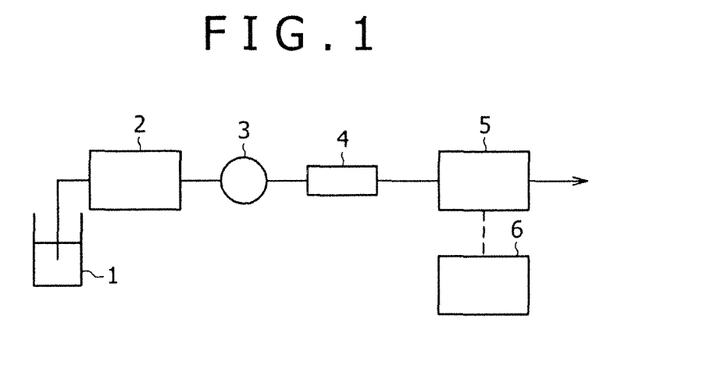
FIG. 1 is a schematic diagram showing an example of the general structure and flow path of liquid chromatographs.

A liquid chromatograph, which is shown in FIG. 1, is equipped with an analytical flow path consisting of an eluent holder 1, an eluent feeder 2, a separator 4, and a detector 5. The eluent feeder 2 feeds an eluent from the eluent feeder 2 to the separator 4.

The analytical flow path has a sample injector 3 placed between the eluent feeder 2 and the separator 4 (including a separation column). The sample injector 3 injects a sample into the flowing eluent, so that the sample is separated into components in the separator 4 and the separated components are detected by the detector 5.

The liquid chromatograph is usually constructed of several units, such as a pump (as the eluent feeder 2), an autosampler (as the sample injector 3), a separation column (as the separator 4), and a detector (as the detector 5).

The autosampler as the sample injector 3 is recently dominated by that of direct injection type. The autosampler of direct injection type causes the inside of the needle to constitute a part of the analytical flow path while the eluent is being fed under a high pressure for analysis.

The autosampler of direct injection type injects a sample in the following manner. First, the needle is detached from the analytical flow path under high pressure, and the detached needle functions as a part of the sample introduction flow path in the autosampler. The sample introduction flow path, which is connected to a syringe to suck up and discharge a sample in the autosampler, sucks up a sample through the needle as the plunger of the syringe is pulled out. After sample sucking, the sample introduction flow path, which holds the sample sucked up through the needle, is switched such that the analytical flow path for the eluent to flow from the pump communicates with the analytical flow path connected to the separation column and the sample held in the sample introduction flow path is injected into the analytical flow path. The autosampler of direct injection type employs a valve to switch the analytical flow path and the sample introduction flow path. It is common practice to place one valve each in the flow paths upstream and downstream the needle.

An ordinary autosampler of direct injection type performs sample injection in a manner which is explained below with reference to FIGS. 2 and 3.

Figure 2:
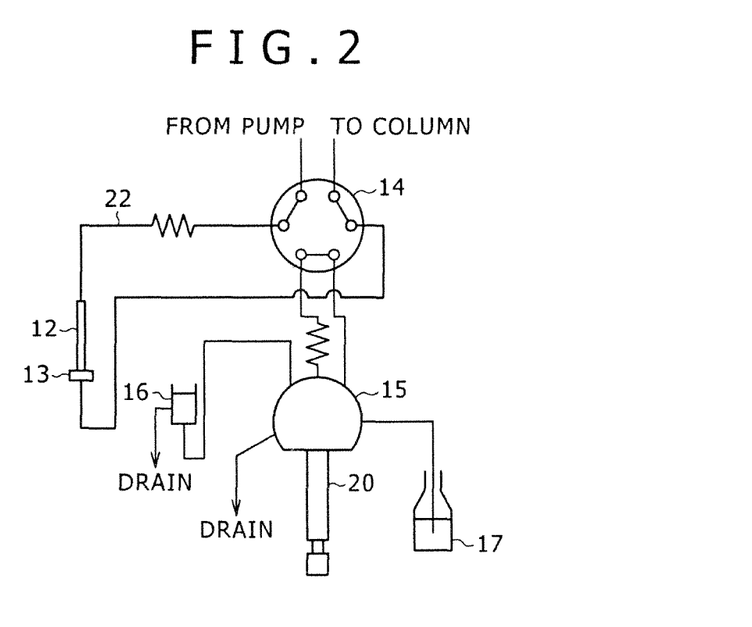
FIG. 2 is a schematic diagram showing an example of the flow path in an ordinary autosampler of direct injection type, the flow path working to discharge a sample from the sample introduction flow path or being in an idle state.

In an ordinary autosampler of direct injection type, the flow path takes the route shown in FIG. 2 when a sample is discharged or sampling is not performed. The eluent delivered from the pump passes through the valve A 14 and then the needle 12. The eluent passes further through the injection port 13 and the valve A 14 again and flows toward the separation column.

Figure 3:
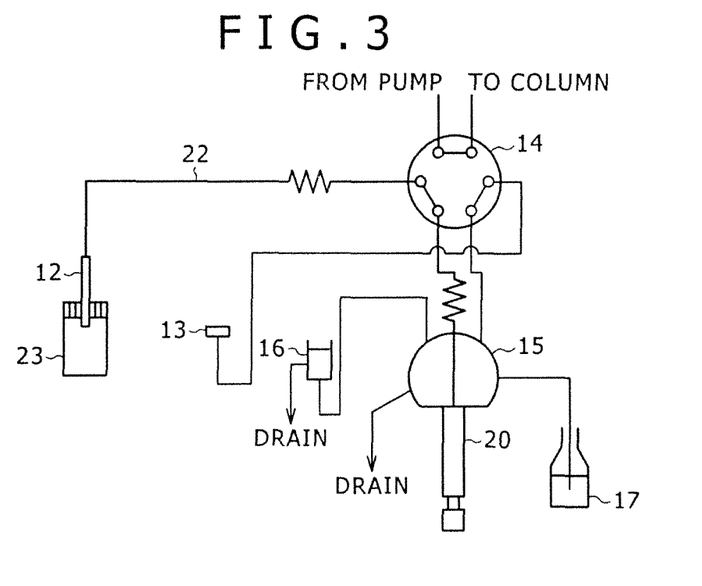
FIG. 3 is a schematic diagram showing an example of the flow path in an ordinary autosampler of direct injection type, the flow path sucking up a sample into the sample introduction flow path.

Also, in an ordinary autosampler of direct injection type, the flow path takes the route shown in FIG. 3 when a sample is sucked up. At the time of sample suction, the valve A 14 acts to switch the flow path. The pump's action causes the eluent being delivered from the pump to flow directly to the separation column without passing through the needle 12 and the injection port 13. After separation from the flow path to the separation column, the needle 12 and the sample loop 22 are connected to the syringe 20 which moves the liquid in the autosampler. With the needle 12 inserted into the vial 23, the syringe 20 sucks up the sample so that the sample is held in the needle 12 and the sample loop 22.

After sample sucking, the needle 12 is connected to the injection port 13, and then the valve A 14 is switched again so that the flow path takes the previous route shown in FIG. 2. As the result, the eluent delivered from the pump enters the sample loop 22 and the needle 12, and the sample held in the needle 12 and the sample loop 22 is pushed into the injection port 13. Thus, the sample flows through the injection port 13 and the valve A 14 to reach the separation column.

As mentioned above, an autosampler of direct injection type is constructed such that both the upstream side and the downstream side of the needle are connected to the valve. This construction is disclosed in Patent Documents 1 and 2 below.

Patent Document 1

Japanese Patent Laid-open No. 2007-121192

Patent Document 2

Japanese Patent Laid-open No. 2005-265805

The autosampler of direct injection type, which is used for the sample injector 3, has a valve to switch the analytical flow path and the sample introduction flow path, the valve being placed at the upstream and downstream sides of the needle.

The disadvantage of the autosampler of direct injection type mentioned above is the necessity of more than one valve. Valves increase the dead volume which deteriorates the accuracy of analysis.

"Dead volume" means any space which exists in the flow from sample introduction to detection in the liquid chromatograph and which is useless, or rather harmful, to sample separation and hence is undesirable.

The dead volume has the following two adverse effects.

First, the dead volume diffuses the sample in the eluent, which results in the broadening of the detected peak.

The diffusion of the sample also reduces the theoretical plate number N (defined below) which is an index to represent the separation characteristics of the column.

$$N = 5.54 \times t_R^2 / W_{0.5h}^2$$

where, $t_R$ retention time $W_{0.5h}^2$: peak width at the middle of peak height Moreover, the diffusion of the sample might mix again the zones of compounds purposely separated by the column.

Second, the dead volume increases the amount of carry-over or tends to cause carry-over.

"Carry-over" means a previously analyzed sample that remains in the liquid chromatograph to be detected in the subsequent analysis.

This is attributable to the dead space that exists at the joint between the pipe and the part or the valve. (There is no complete adhesion between the surface of the inserted pipe and the surface of the pipe receiver, and the gap between the surfaces forms the dead space.) The injected sample remains in the dead space and the remaining sample leaks out during subsequent analyses.

For these reasons, one of the important factors to improve the accuracy of analysis is how to reduce dead space in the analytical flow path from the autosampler to the separation column and from the separation column to the detector.

The conventional method of achieving the foregoing object is by using as thin a pipe as permissible (from the standpoint of flow rate and pressure) for the analytical flow path and also by using parts with a minimum area in contact with the liquid (thereby eliminating unnecessary spaces).

However, there is a limit to reducing the inside diameter and length of the pipe and changing the shape of parts to reduce dead volume.

OBJECT AND SUMMARY OF THE INVENTION

It is an object of the present invention to provide a liquid chromatograph and a sample introducing apparatus, which are capable of reducing carry-over easily by a simple structure without resorting to reducing the length and inside diameter of the pipe and contriving the shape of parts.

The gist of the present invention resides in a sample introducing apparatus intended to introduce a sample from a sample introduction flow path into a chromatograph equipped with a liquid feeding unit to deliver an eluent and an analytical flow path including a separator, which includes a sample sucking means for sucking up the sample, a flow path switching means for switching the separation and connection of the analytical flow path and the sample introduction flow path including a needle, and a control means for controlling the action of the sample sucking means and the flow path switching means, with the flow path switching means communicating with the upstream side of the needle and the separator communicating with the downstream side of the needle without the flow path switching means interposed between them.

The sample introducing apparatus according to the present invention is designed such that the analytical flow path runs from the needle to the separation column without the flow path switching means placed at the downstream side of the needle. This design reduces dead volume, which in turn reduces the diffusion of the sample injected into the analytical flow path.

Moreover, the absence of the flow path switching means at the downstream side of the needle to inject a sample into the analytical flow path eliminates connection of the pipe with the flow path switching means. This prevents the sample from remaining in the connecting part, thereby reducing sample carry-over.

In addition, the sample introducing apparatus according to the present invention does not need much modification of the conventional autosampler of direct injection type and hence it can be constructed and realized easily.

DESCRIPTION OF THE PREFERRED EMBODIMENTS

The embodiments of the present invention will be described below with reference to the accompanying drawings.

The First Embodiment

Figure 4:
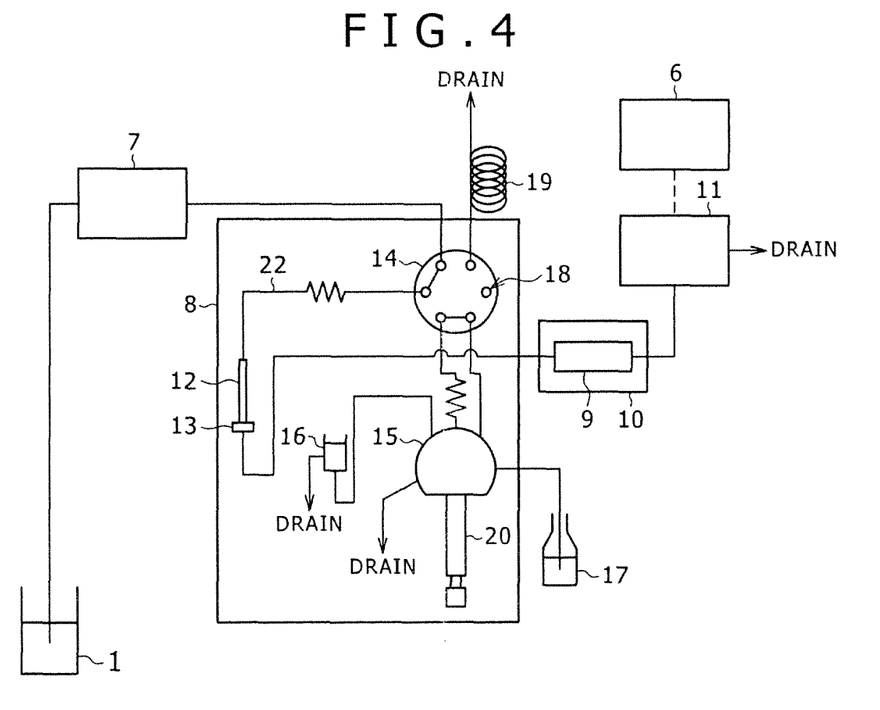
FIG. 4 is a schematic diagram showing an example of the liquid chromatograph according to one embodiment of the present invention.

FIG. 4 shows an example of the liquid chromatograph according to the present invention.

The eluent holder 1 is connected to the pump 7 through a pipe. The pump 7 sucks and delivers the eluent. The down stream side of the pump 7 is connected to the autosampler 8.

The autosampler 8 consists of the needle to suck up and discharge samples, the injection port 13 communicating with the separation column, the valve A 14 to switch the flow path (as the flow path switching means), the valve B 15, the syringe 20 to deliver the liquid in the autosampler, and the washing port 16 to clean the needle 12 of contaminants. (The outer wall of the needle is contaminated with a sample when the needle is inserted into the vial 23 to suck up a sample.)

With the tip of the needle 12 inserted into the vial 23 holding a sample, the syringe 20 sucks up the sample into the needle 12. The sample which has been sucked up is held temporarily in the needle 12 and the sample loop 22 communicating with the needle 12. Incidentally, the needle 12 and the sample loop 22 are collectively called the sample introduction flow path.

With the needle 12 moved to the injection port 13, the valve A 14 (flow path switching means) switches so that the flow path from the pump communicates with the needle 12 and the injection port 13. As the result, the eluent delivered from the pump enters the sample loop 22 and the needle 12 and the sample held in the sample loop 22 and the needle 12 enters the separation column 9 through the injection port 13.

As mentioned in the section of prior art, the valve A 14 to switch the flow path connects and separates the sample introduction flow path (including the needle) to and from the analytical flow path. As the valve A 14 separates the sample introduction flow path from the analytical flow path, the sample introduction flow path communicates with the syringe 20, so that the syringe 20 sucks up the sample. Except when the sample is sucked up, the valve A 14 keeps the sample introduction flow path connected to the analytical flow path, with the sample introduction flow path constituting a part of the analytical flow path.

The needle 12, the syringe 20, and the autosampler 8 are collectively referred to as the sample sucking means.

The valve A 14, the valve B 15, and the autosampler 8 work under control by the control means (not shown).

The valve A 14 has six connecting holes, with one closed by the plug 18 and one connected to the resistance coil 19 (which serves also as a drain pipe). (Closing with the plug 18 is not necessary if the valve A 14 has five connection holes.) The valve B 15 has a pipe connected thereto which passes the cleaning solution 17.

The analytical flow path extending from the pump 7 passes through the valve A 14 (in its upstream side of the needle 12) and also passes through the injection port 13 (instead of passing through the valve A 14) to reach the separation column 9, which is placed in the column oven 10, (in its downstream side of the needle 12). The analytical flow path passing through the separation column 9 connects with the detector 11 and the data processing unit 6 sequentially.

Figure 5:
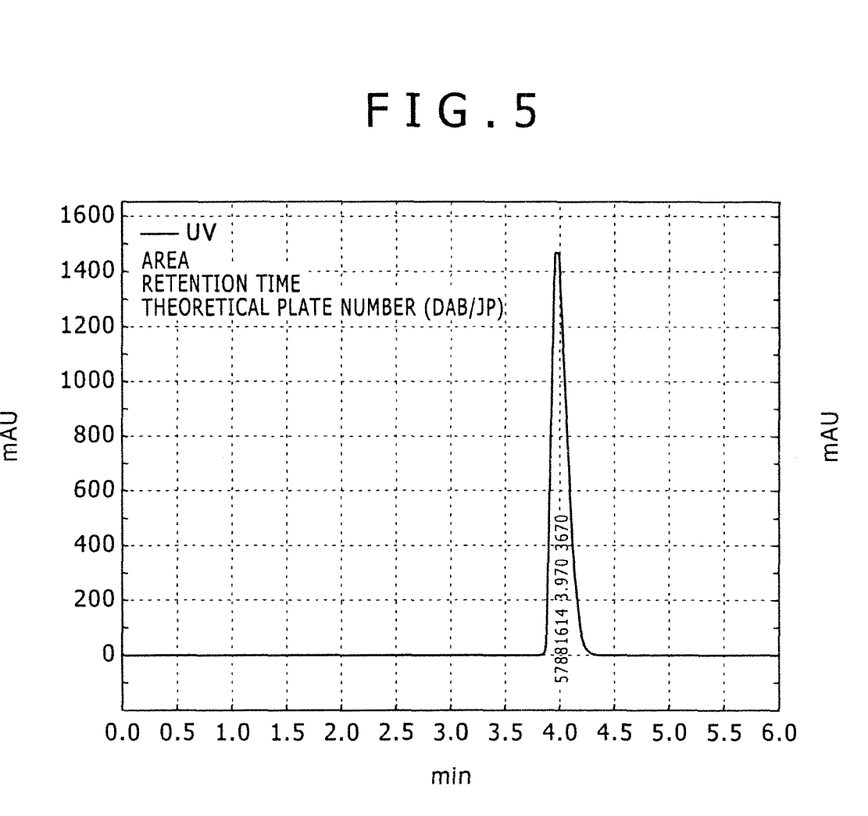
FIG. 5 is a chromatogram of methylparaben (600 mg/L dissolved in 60% methanol) obtained by using an ordinary autosampler of direct injection type.
Figure 6:
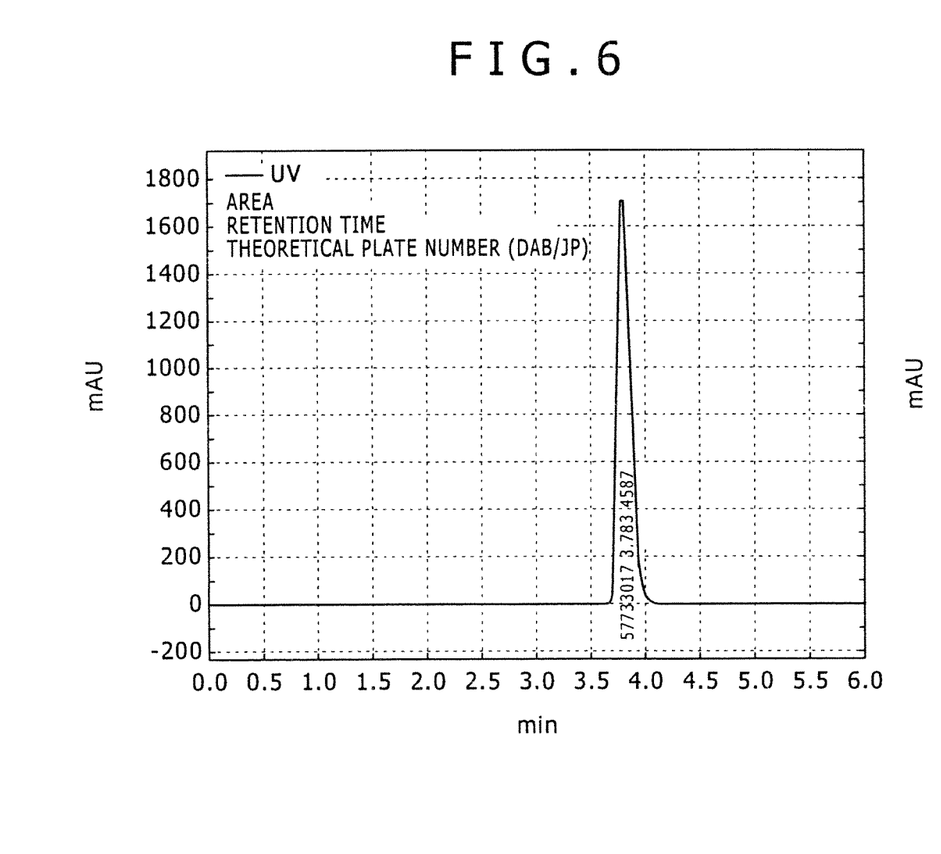
FIG. 6 is a chromatogram of methylparaben (600 mg/L dissolved in 60% methanol) obtained by using an autosampler according to one embodiment of the present invention.

An analysis was performed on methylparaben (600 mg/L dissolved in 60% methanol) by using an ordinary autosampler of direct injection type. The resulting chromatogram is shown in FIG. 5. The same analysis as above was performed by using the liquid chromatograph (mentioned above) in which the liquid flows from the needle 12 without passing through the valve. The resulting chromatogram is shown in FIG. 6.

The two chromatograms (shown in FIGS. 5 and 6) differ in the theoretical plate number which denotes the sharpness of the measured peak. The former has a value of 3670, whereas the latter has a value of 4587 (both shown at the top). This result apparently shows that the chromatograph according to the present invention retains a higher value of theoretical plate number.

The amount of carry-over was determined by injection of 60% methanol after analysis of methylparaben (600 mg/L dissolved in 60% methanol). Experiments were carried out with an ordinary autosampler of direct injection type and the liquid chromatograph according to the present invention. The resulting chromatograms are shown in FIGS. 7 and 8, respectively.

Figure 7:
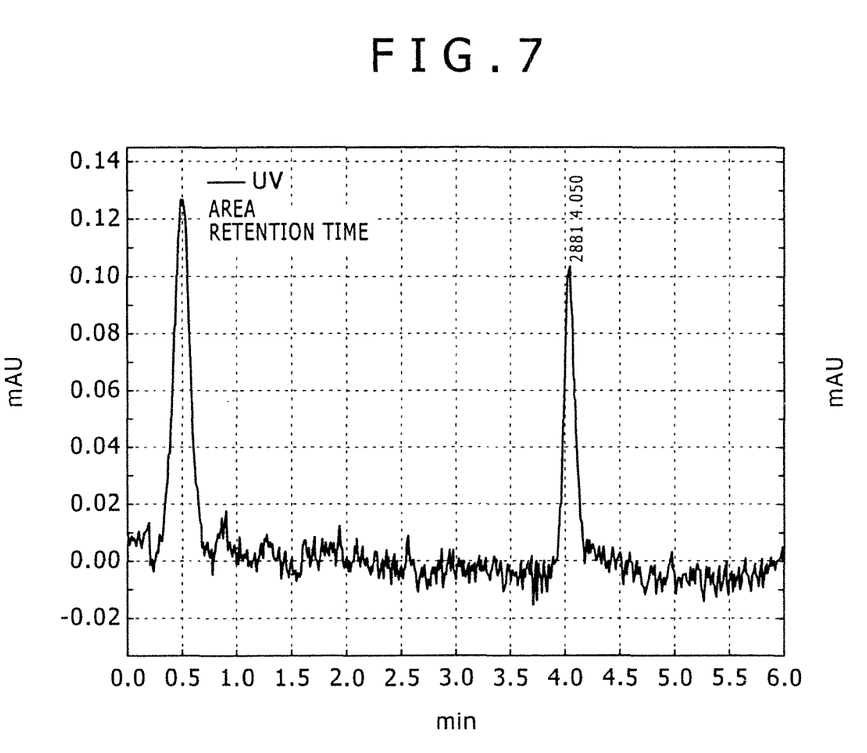
FIG. 7 is a chromatogram showing carry-over induced by introduction of 60% methanol after the analysis of methylparaben (600 mg/L dissolved in 60% methanol) which was carried out by using an ordinary autosampler of direct injection type.

The amount of carry-over was obtained from FIGS. 5 and 7 in an experiment with an ordinary autosampler of direct injection type. The thus obtained amount of carry-over is 0.0050%.

Figure 8:
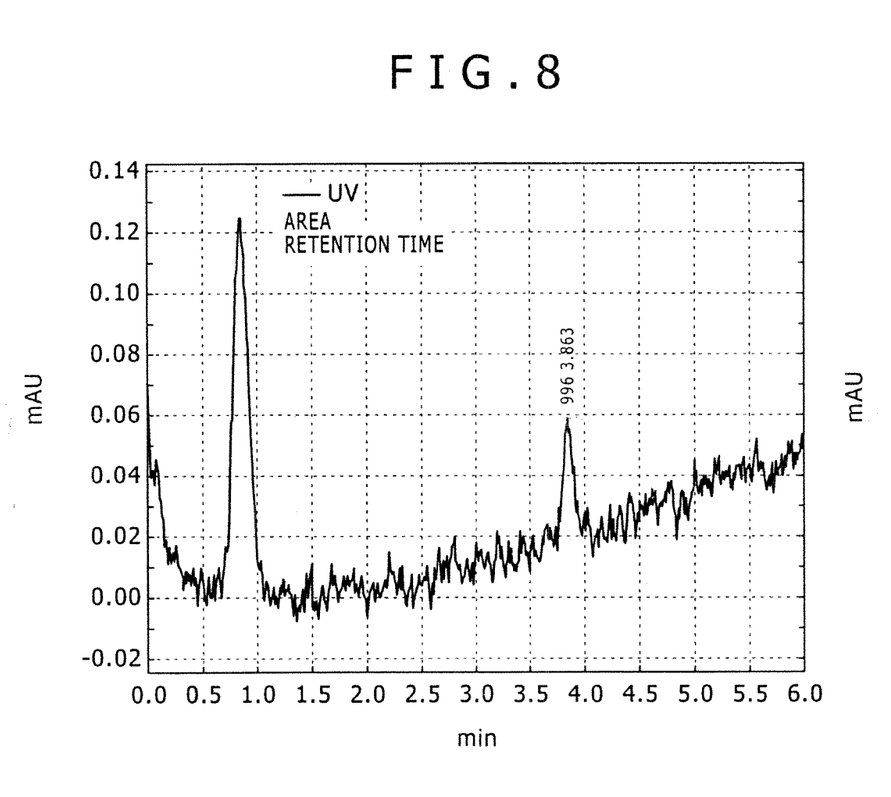
FIG. 8 is a chromatogram showing carry-over induced by introduction of 60% methanol after the analysis of methylparaben (600 mg/L dissolved in 60% methanol) which was carried out by using an autosampler according to one embodiment of the present invention.

By contrast, the amount of carry-over was obtained from FIGS. 6 and 8 in an experiment with the liquid chromatograph according to the present invention. The thus obtained amount of carry-over is 0.0017%. The foregoing suggests that it is possible to reduce the amount of carry-over by using the liquid chromatograph according to the present invention.

In other words, the liquid chromatograph according to the present invention is simple in structure and yet is capable of reducing the amount of carry-over.

Figure 9:
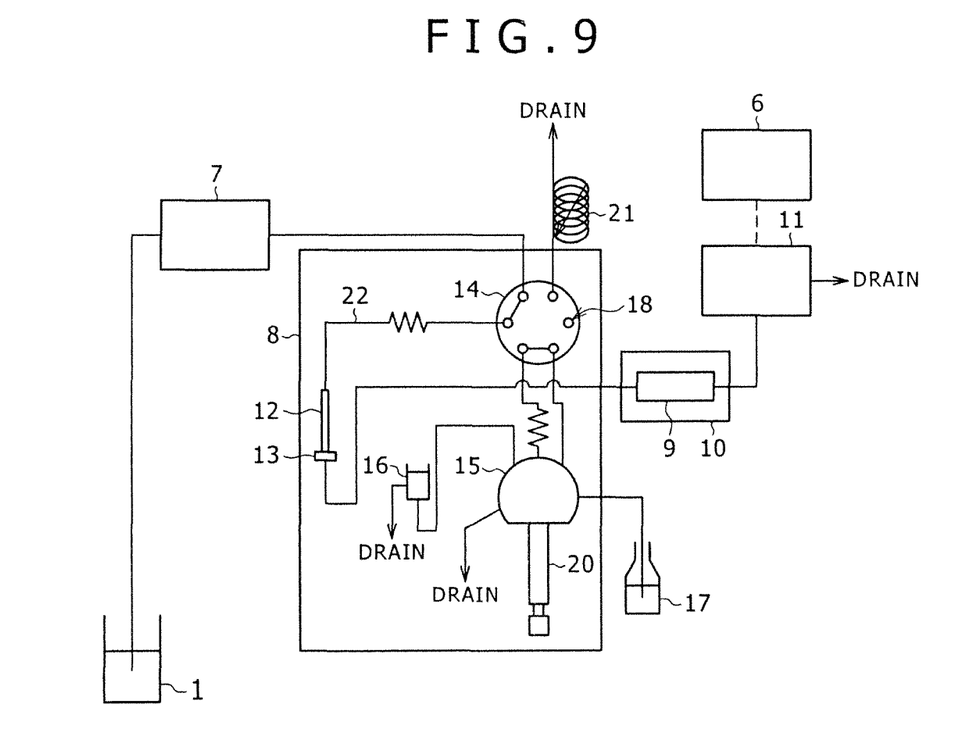
FIG. 9 is a schematic diagram showing an example of another liquid chromatograph according to one embodiment of the present invention (having the switching means provided with a means for adjusting the flow rate resistance).

The above-mentioned embodiment of the present invention may be modified such that the valve A 14 is provided with the coil 12 to control the flow path resistance as shown in FIG. 9. The coil capable of changing the flow path resistance reduces the fluctuation of pressure that occurs when the flow path is switched, thereby stabilizing the base line.

The Second Embodiment

This embodiment demonstrates how the present invention produces its effect when applied to a conventional nanoflow liquid chromatograph disclosed in Japanese Patent No. 3823092.

Figure 10:
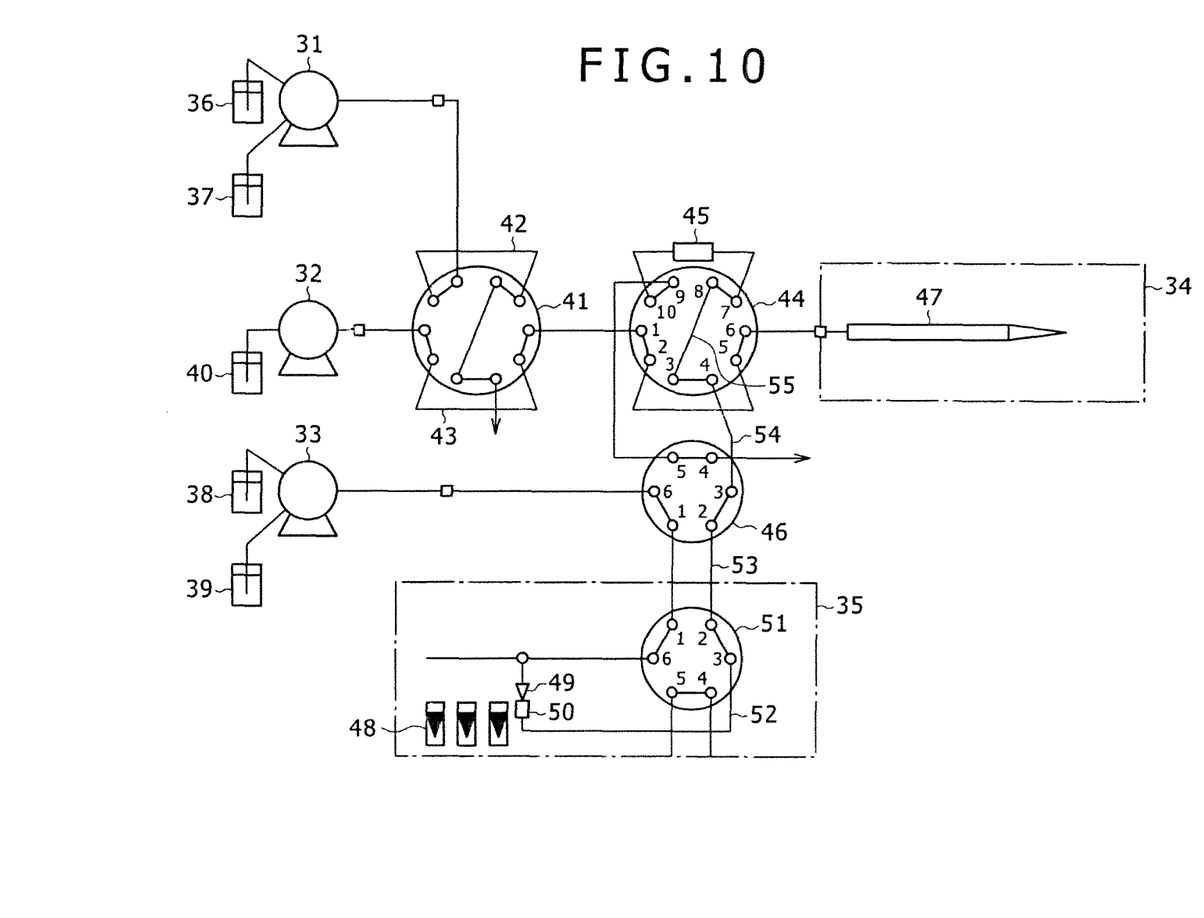
FIG. 10 is a schematic diagram showing the structure of the conventional liquid chromatograph which is referenced for comparison in the second embodiment of the present invention.

This liquid chromatograph is that of trap column type, which is constructed as shown in FIG. 10.

It has the gradient pump 31, the nanoflow pump 32, and the loading pump 33, whose flow rates are respectively tens to hundreds of μL/min, tens to hundreds of nL/min, and several to ten-odd μL/min.

It also has the 10-way valve 41 and the injection valve 44 (to switch the trap column), each having ten ports and taking two positions. It also has the backlash valve 46 and the sampler valve 51 (to switch the flow path), each having six ports and taking two positions.

It permits the sample 48 to be sucked up into the needle 49 by a metering device (not shown) in the autosampler 35, in such a way that fluid-tightness is ensured between the tip of the needle 49 and the injection port 50. Incidentally, pipes are numbered 52, 53, 54, 55, and 56.

Operation proceeds as follows. First, the sample 48 is sucked up into the needle 49. Then, the sample 48 is delivered to the trap column 45 by the loading pump 33 through the pipes 52, 53, 54, and 55 and the flow path switching valves 51, 46, and 44. The eluents 36 and 37 are mixed together by the gradient pump 31, and the mixture of eluents is delivered to the loop 42 and the loop 43 alternately by the 10-way valve 41 which is switched periodically.

The mixture of the eluents 36 and 37 and part of the water 40, which have been delivered to the loops 42 and 43, are forced into the port 1 of the injection valve 44 by the nanoflow pump 32. This procedure realizes the nanoflow gradient liquid delivery at such low a flow rate as tens to hundreds of nL/min.

If desalting is necessary for the sample 48 held in the trap column 45, the backlash valve 46 is switched so that the ports 5 and 6 are connected to each other (not shown) and the eluents 38 and 39 are delivered to the trap column 45.

As the injection valve 44 is switched, so that the ports 1 and 10 are connected to each other and the ports 6 and 7 are connected to each other (not shown), the sample 48 which has been held in the trap column 45 is eluted into the separation column 47 by the nanoflow gradient liquid delivery mentioned above. The eluate is analyzed by the mass spectrometer 34.

Figure 11:
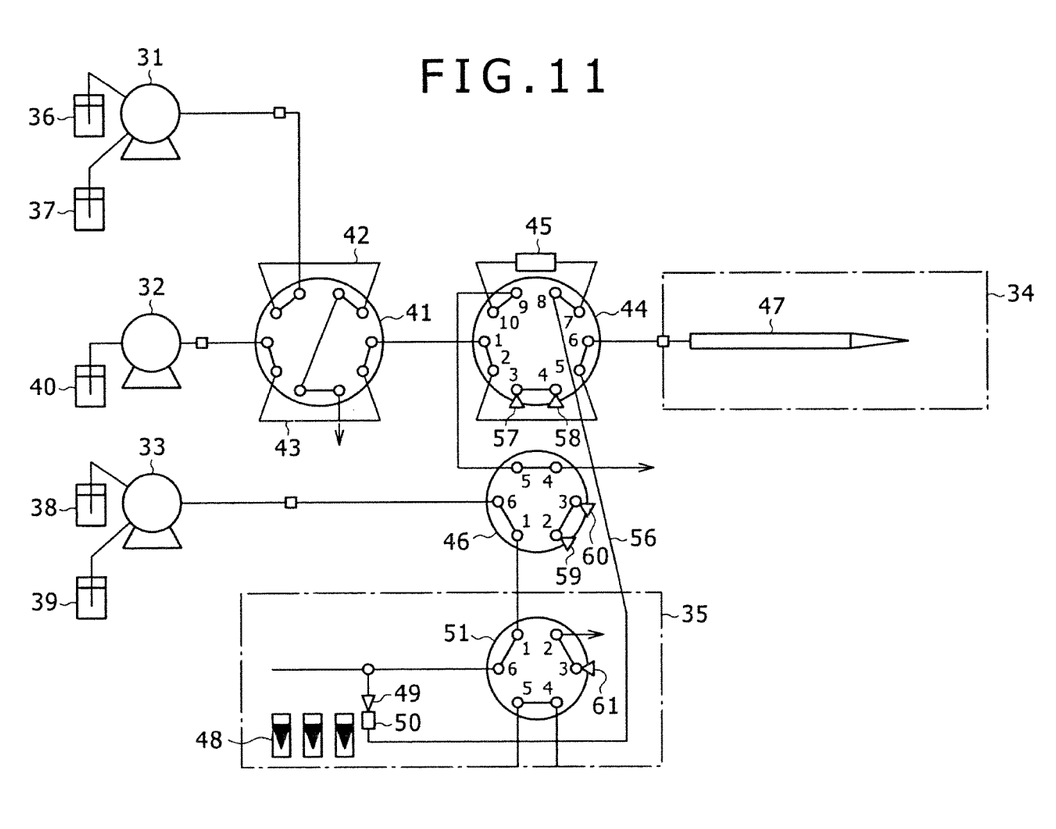
FIG. 11 is a schematic diagram showing the structure of the liquid chromatograph according to the second embodiment of the present invention.

In the second embodiment, the conventional liquid chromatograph shown in FIG. 10 is modified as shown in FIG. 11 according to the present invention.

The modified chromatograph is constructed such that the injection port 50 of the autosampler 35 is connected to the port 8 of the injection valve 44 (to switch the trap column) directly through the pipe 56. Incidentally, the numerals 57, 58, 59, 60, and 61 denote closing plugs.

Eliminating the pipes used in the conventional analyzer greatly reduces the dead volume in the loading flow path from the injection port 50 to the trap column 45. The result is that the spreading of the sample 48 in the flow path decreases and the loading time required for the sample 48 to be delivered to the trap column 45 decreases.

Figure 12:
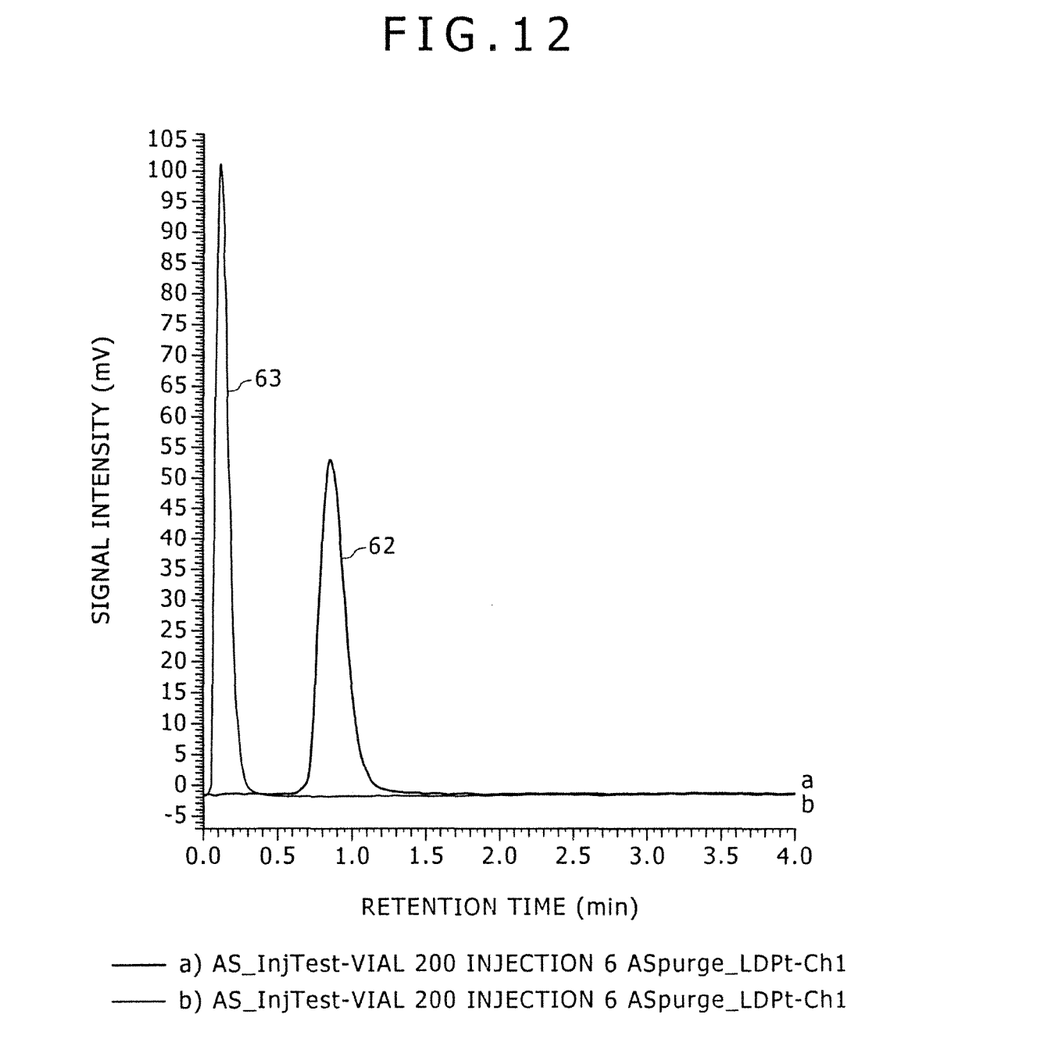
FIG. 12 is a diagram showing the sample band in the flow path according to the conventional technology and one embodiment of the present invention.

The conventional and modified liquid chromatographs shown in FIGS. 10 and 11 were tested for the spreading of the sample 48 in the flow path and the loading time. The results are shown in FIG. 12. Incidentally, the modified one is constructed such that the piping to the port 8 of the injection valve 44 (to switch the trap column) is connected directly to a UV absorptiometer.

The foregoing test was carried out under the following conditions.
Flow rate of the loading pump 33: 10 μL/min
Wavelength for detection by the UV absorptiometer: 214 nm
Sample: angiotensin The numerals 62 and 63 in FIG. 12 represent respectively the band of the sample measured by using the conventional chromatograph shown in FIG. 10 and the modified chromatograph shown in FIG. 11. It is noted that the band 63 is taller and narrower than the band 62.

The results shown in FIG. 12 suggest that the foregoing modification greatly improves the separation behavior of liquid chromatography and also greatly reduces the loading time (and hence reduces time required for analysis).

The liquid chromatographs shown in FIGS. 10 and 11 were tested for carry-over that occurs in analysis of enzymatic digests of human serum. The results are shown in FIGS. 13 and 14, respectively.

Figure 13A:
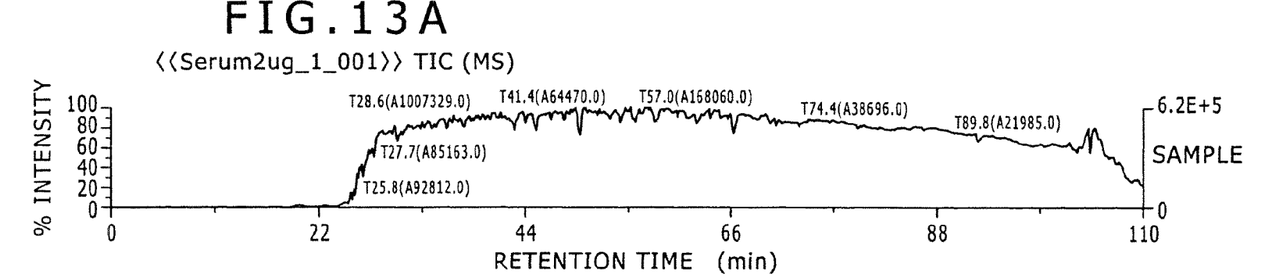
FIG. 13 is a total ion chromatogram pertaining to one embodiment of the present invention.
Figure 13B:
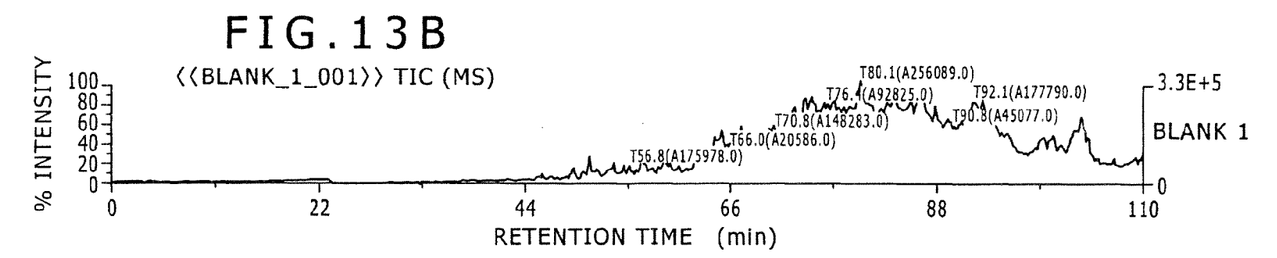
Figure 13C:
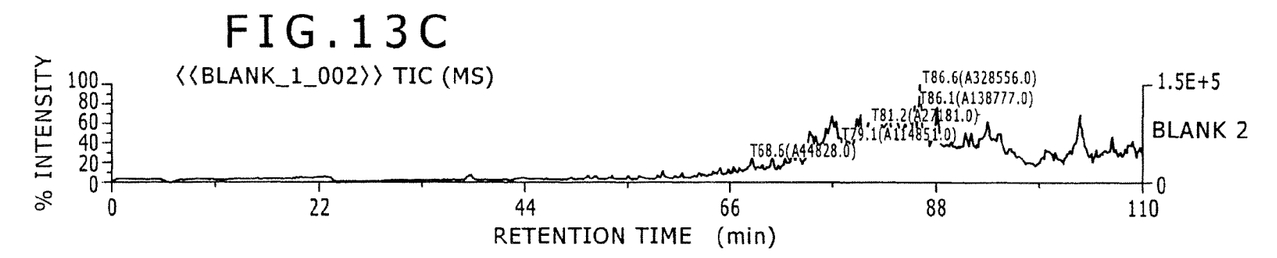
Figure 14A:
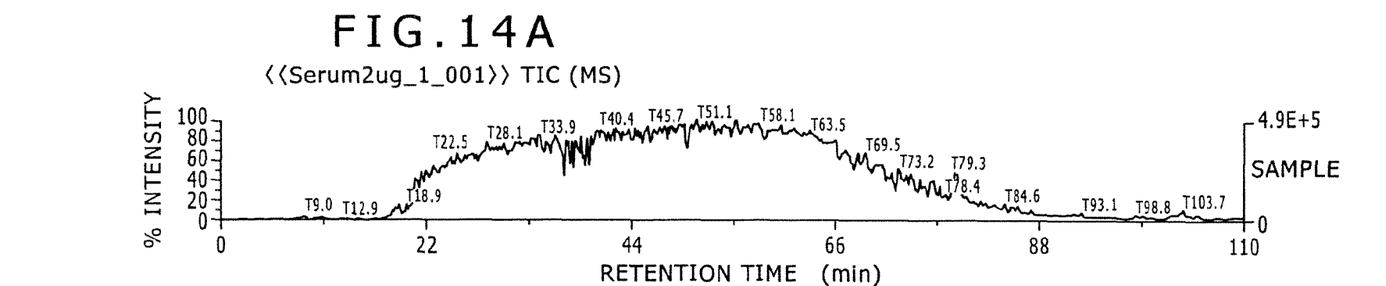
FIG. 14 is a total ion chromatogram pertaining to another embodiment of the present invention.
Figure 14B:
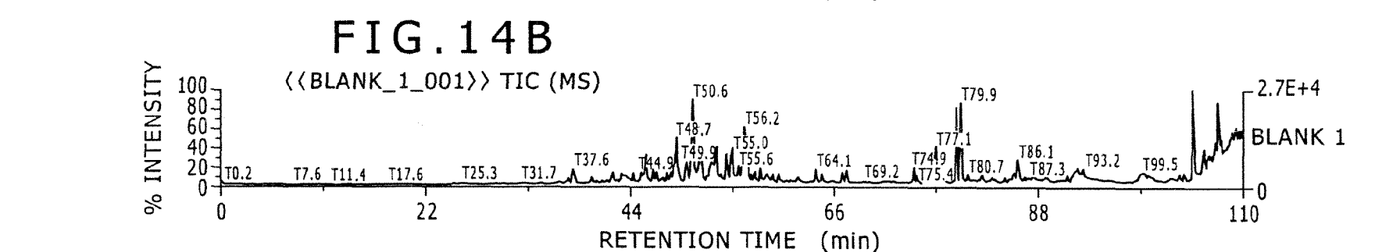
Figure 14C:
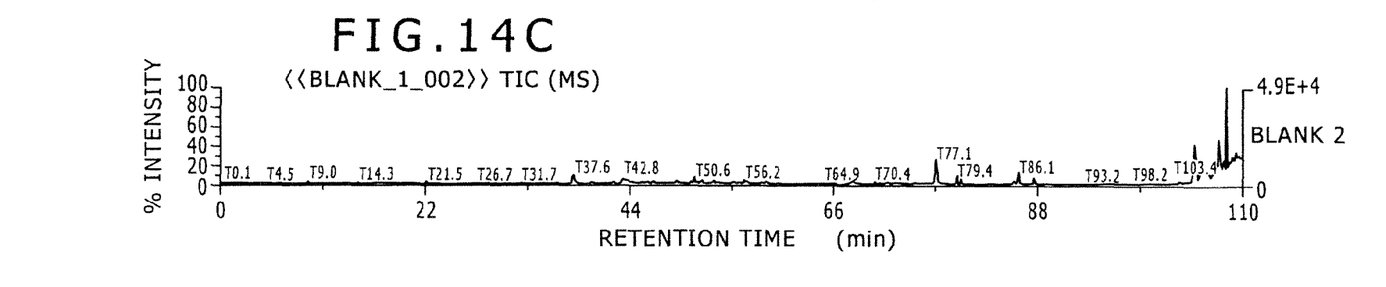

FIGS. 13 and 14 are total ion chromatograms obtained by the mass spectrometer 34. The top represents the chromatogram obtained when the sample was injected. The middle represents the chromatogram of blank obtained for the first time. The bottom represents the chromatogram of blank obtained for the second time.

Carry-over in initial blank test was calculated for a component having a mass-to-charge ratio (m/z) of 825.78, which was selected as an example, by using the conventional and modified chromatographs mentioned above. The conventional one gave a carry-over as high as 34.8%, whereas the modified one gave a carry-over as low as 3.9%.

A probable reason for this is that the conventional chromatograph has the backlash valve 46 in the loading flow path and the connecting parts of the pipes hold the sample, resulting in a large amount of carry-over.

Thus, the embodiment of the present invention solves the problems with carry-over involved in the conventional liquid chromatograph.

What is claimed is:

1. A sample introducing apparatus configured to introduce a sample into a liquid chromatograph equipped with a liquid feeding unit to deliver an eluent, a separation column to receive said eluent and the sample, and a detector to detect said sample supplied from said separation column, said sample introducing apparatus comprising an analytical flow path, wherein said analytical flow path comprises:
   a sample introduction flow path having a needle configured to suction said sample, and a sample injection port in fluid communication with one end of a sample delivery pipe;
   a sample flow path switching device connected to said sample introduction flow path and configured to switch the flow path of said sample, wherein the sample flow path switching device switches a first flow passage and a second flow passage, wherein the first flow passage connects said needle, a sample sucking unit, and a sample retention unit, and the second flow passage connects said liquid feeding unit, said needle, said sample retention unit, said separation column, and said detector, and wherein said sample sucking unit sucks up the sample through the needle, and the sample retention unit retains the sucked sample temporarily; and
   a trap column injection valve configured to switch the flow paths of the eluent and the sample, wherein the other end of said sample delivery pipe is in fluid communication with a port of said trap column injection valve such that said sample injection port and said trap column injection valve are in direct fluid communication with each other without passing through said sample flow path switching device.

2. The sample introducing apparatus of claim 1, wherein said sample introduction flow path is fluid communication with said sample injection port.

3. The sample introducing apparatus of claim 1, wherein said liquid feeding unit is configured to deliver at least two eluents.

4. The sample introducing apparatus of claim 3, wherein said liquid feeding unit is configured to connect to said trap column injection valve via a ten-way valve.

5. The sample introducing apparatus of claim 4, wherein said ten-way valve is further connected to a water feeding unit.

6. The sample introducing apparatus of claim 1, wherein said liquid feeding unit is configured to connect to said trap column injection valve via a ten-way valve.

7. A liquid chromatograph comprising:
   a liquid feeding unit to deliver an eluent;
   a separation column to receive said eluent and a sample;
   a detector to detect said sample supplied from said separation column; and
   an analytical flow path, wherein said analytical flow path comprises:
      a sample introduction flow path having a needle configured to suction said sample, and a sample injection port in fluid communication with one end of a sample delivery pipe;
      a sample flow path switching device connected to said sample introduction flow path and configured to switch the flow path of said sample, wherein the sample flow path switching device switches a first flow passage and a second flow passage, wherein the first flow passage connects said needle, a sample sucking unit, and a sample retention unit, and the second flow passage connects said liquid feeding unit, said needle, said sample retention unit, said separation column, and said detector, and wherein said sample sucking unit sucks up the sample through the needle, and the sample retention unit retains the sucked sample temporarily; and
      a trap column injection valve configured to switch the flow paths of the eluent and the sample, wherein the other end of said sample delivery pipe is in fluid communication with a port of said trap column injection valve such that said sample injection port and said trap column injection valve are in direct fluid communication with each other without passing through said sample flow path switching device.

8. The liquid chromatograph of claim 7, wherein said sample introduction flow path is fluid communication with said sample injection port.

9. The liquid chromatograph of claim 7, wherein said liquid feeding unit is configured to deliver at least two eluents.

10. The liquid chromatograph of claim 9, wherein said liquid feeding unit is configured to connect to said trap column injection valve via a ten-way valve.

11. The liquid chromatograph of claim 10, wherein said ten-way valve is further connected to a water feeding unit.

12. The liquid chromatograph of claim 7, wherein said liquid feeding unit is configured to connect to said trap column injection valve via a ten-way valve.

13. A sample introducing apparatus configured to introduce a sample into a liquid chromatograph equipped with a liquid feeding unit to deliver an eluent, a separation column to separate the introduced sample, and a detector to detect the separated sample, comprising:
 a needle;
 a sample sucking unit to suck up the sample through said needle;
 a sample retention unit to retain the sucked sample temporarily;
 a sample injection port;
 a first flow passage connecting said needle and said sample retention unit;
 a second flow passage connecting said sample sucking unit, said needle, and said sample retention unit;
 a third flow passage connecting said liquid feeding unit, said needle, said sample retention unit, said separation column, and said detector;
 a flow path switching unit to switch said second flow passage and said third flow passage; and
 a control unit to control the action of said needle, said sample sucking unit, and said flow path switching unit;
 wherein said control unit configured for
  retaining said sample into said sample retention unit in said second flow passage,
  connecting said needle and sample injection port while said sample is retained in said sample retention unit, and
  switching from said second flow passage to said third flow passage to introduce the retained sample into said separation column through said sample injection port after said needle and said sample injection port are connected,
 wherein said flow path switching unit is located upstream of said needle in the switched third flow passage, and
 wherein said sample injection port is communicated with said separation column without going through said flow path switching unit in said third flow passage.

14. A liquid chromatograph including a pump to deliver an eluent, a sample introducing apparatus to introduce a sample into the delivered eluent, a separation column to separate the introduced sample, a detector to detect the separated sample, comprising:
 a needle;
 a sample sucking unit to suck up the sample through said needle;
 a sample retention unit to retain the sucked sample temporarily;
 a sample injection port;
 a first flow passage connecting said needle and said sample retention unit;
 a second flow passage connecting said sample sucking unit, said needle, and said sample retention unit;
 a third flow passage connecting said liquid feeding unit, said needle, said sample retention unit, said separation column, and said detector;
 a flow path switching unit to switch said second flow passage and said third flow passage; and
 a control unit to control the action of said needle, said sample sucking unit, and said flow path switching unit;
 wherein said control unit configured for
  retaining said sample into said sample retention unit,
  connecting said needle and said sample injection port while said sample is retained in said sample retention unit, and
  switching from said second flow passage to said third flow passage to introduce the retained sample into said separation column through said sample injection port after said needle and said sample injection port are connected,
 wherein said flow path switching unit is located upstream of said needle in the switched third passage, and
 wherein said sample injection port is communicate with said separation column without going through said flow path switching unit in the switched third flow passage.

15. A sample introducing apparatus configured to introduce a sample into a liquid chromatograph equipped with first and second liquid feeding units to deliver an eluent, a trap column to trap the introduced sample, a separation column to separate the sample passed said trap column, and a detector to detect the separated sample, comprising:
 a needle;
 a sample sucking unit to suck up the sample through said needle;
 a sample retention unit to retain the sucked sample temporarily;
 a sample injection port;
 a first flow passage connecting said needle and said sample retention unit;
 a second flow passage connecting said sample sucking unit, said needle, and said sample retention unit;
 a third flow passage connecting said first liquid feeding unit, said needle, said sample retention unit, said sample injection port, and said trap column;
 a fourth flow passage connecting said second liquid feeding unit, said trap column, said separation column, and said detector;
 a flow path switching unit to switch said second flow passage and said third flow passage;
 a trap column valve including said trap column to switch said third flow passage and said fourth flow passage; and
 a control unit to control the action of said needle, said sample sucking unit, said flow path switching unit, and said trap column valve:
 wherein said control unit is configured for
  retaining said sample into said sample retention unit in said second flow passage,
  connecting said needle and said sample retention unit while said sample is retained in said sample retention unit,
  switching from said second flow passage to said third flow passage to introduce the retained sample into the trap column through said sample injection port after said needle and said sample injection port are connected, and
  switching from said third flow passage to said forth flow passage while the sample is trapped in said trap column,
 wherein said flow path switching unit is located upstream of said needle in the switched third flow passage, and
 wherein said sample injection port is communicated with said trap column without going through said flow path switching unit in said third flow passage.

16. A liquid chromatograph including first and second pump to deliver an eluent, a sample introducing apparatus to introduce the sample into the delivered eluent, a trap column to trap the introduced sample, a separation column to separate the sample passed through said trap column, a detector to detect the separated sample, comprising:
- a needle;
- a sample sucking unit to suck up the sample through said needle;
- a sample retention unit to retain the sucked sample temporarily;
- a sample injection port;
- first flow passage connecting said needle and said sample retention unit;
- a second flow passage connecting said sample sucking unit, said needle, and said sample retention unit;
- a third flow passage connecting said first liquid feeding unit, said needle, said sample retention unit, said sample injection port, and said trap column;
- a fourth flow passage connecting said second liquid feeding unit, said trap column, said separation column, and said detector;
- a flow path switching unit to switch said second flow passage and said third flow passage;

a trap column valve including said trap column to switch said third flow passage and said fourth flow passage; and a control unit to control the action of said needle, said sample sucking unit, said flow path switching unit, and trap column valve;

wherein said control unit is configured for
- retaining said sample into said sample retention unit in said second flow passage,
- connecting said needle and said sample injection port while said sample is retained in said sample retention unit,
- switching from said second flow passage to said third flow passage to introduce the retained sample into said trap column through said sample injection port after said needle and said sample injection port are connected, and
- switching from said third flow passage to said fourth flow passage while said trap sample is trapped in said trap column, wherein said flow path switching unit is located upstream of said needle in the switched third flow passage, and wherein said sample injection port is communicated with said trap column without going through said flow path switching unit in said third flow passage.

* * * * *